United States Patent [19]

Neisius et al.

[11] 4,029,597

[45] June 14, 1977

[54] NON-BLEEDING INDICATORS AND DYES THEREFOR USED IN pH DETERMINATION PROCESS

[75] Inventors: Karlheinz Neisius; Wilhelm Bäumer, both of Darmstadt, Germany

[73] Assignee: E. Merck A. G., Darmstadt, Germany

[22] Filed: Aug. 6, 1975

[21] Appl. No.: 602,470

Related U.S. Application Data

[62] Division of Ser. No. 807,411, March 14, 1969.

[52] U.S. Cl. .......................... 252/408; 23/253 TP; 260/200; 428/411
[51] Int. Cl.² ................. G01N 31/00; G01N 33/00
[58] Field of Search ................. 428/411; 260/200; 23/253 TP, 230 R; 252/408

[56] References Cited

UNITED STATES PATENTS

| 2,806,023 | 9/1957 | Wenker | 260/200 |
| 3,202,652 | 8/1965 | Meininger | 260/200 |

FOREIGN PATENTS OR APPLICATIONS

| 1,256,445 | 6/1968 | Germany |

Primary Examiner—Marion E. McCamish
Attorney, Agent, or Firm—Millen & White

[57] ABSTRACT

In colorimetric indicators comprising a carrier such as cellulose saturated with one or more azo dyes having reactive groups capable of forming a chemical bond with the carrier material, the improvement wherein the indicator is made non-bleeding by using such dyes which, in addition to the reactive group, contain at least one additional sulfonic acid and/or carboxylic acid group, an example of such a dye being 4-anilino-3'-(2-hydroxysulfonyloxyethylsulfonyl)-azobenzene-6'-carboxylic acid.

53 Claims, No Drawings

NON-BLEEDING INDICATORS AND DYES THEREFOR USED IN pH DETERMINATION PROCESS

This is a division of application Ser. No. 807,411, filed Mar. 14, 1969.

This invention relates to non-bleeding indicators, such as indicator paper, films, powders and shaped objects which do not run upon contact with aqueous solutions.

In German Published Application [DAS]No. 1,256,445, there are described non-bleeding indicator papers or films comprising cellulose or regenerated cellulose as the carrier and which are saturated with one or more indicator dyes having "reactive groups" which result in chemical bond with the carrier material. As preferred indicator dyes, there are mentioned the coupling products of diazotized sulfuric acid ester of β-(p-aminophenylsulfonyl)-ethanol with α-naphthol, dimethylaniline or phenol.

Without meaning to disparage the contents of the aforesaid German published application, it was discovered that indicator papers made in accordance with the teachings of the patent have serious disadvantages for practical usage. In particular, during the dyeing step, colored by-products are obtained which are neither chemically bound in the fiber nor removable by washing with water. These by-products exhibit a very significant detrimental effect on the quality of the resultant indicator papers.

For example, when coupling the diazotized sulfuric acid ester iof β-(p-aminophenylsulfonyl)-ethanol (disclosed in Example 1 of the German application) wit dimethylaniline, a pigment is obtained which, during the subsequent paper dyeing in the alkaline reaction medium is precipitated to a large part in the form of a product which does not react with the fiber and which, due to its water insolubility, cannot be washed out with water. The paper bleeds severely upon coming into contact with acids. If the water-insoluble by-products produced during the dyeing process are removed by acids or ethanol — a cumbersome procedure — then a paper is obtained which is so pallid that it does not satisfy the requirements of practice.

In a similar manner, the dyes produced by coupling the above-mentioned diazotized sulfuric acid ester with α-naphthol or phenol are, in part, separated during the dyeing process in the form of water-insoluble by-products which do not react with the fiber. These papers bleed upon coming into contact with bases. A non-bleeding paper having a somewhat better chroma than in the first-mentioned case is obtained only after removing the firmly adhering by-products by means of bases or alcohol.

Thus, one aspect of this invention is to provide indicators having improved properties as compared to indicators produced on the basis of the German application.

Another aspect of this invention is to provide novel dyes and methods of making same.

Upon further study of the specification and claims, other objects and advantages of the present invention will become apparent.

To achieve these ends high-chroma papers or films can be manufactured by employing, as the dye indicators, azo dyes containing, in addition to the reactive group, at least one additional sulfonic acid group and-/or carboxylic acid group. When using such azo dyes, the by-products, which heretofore could be removed only with substantial difficulty, can be very readily washed out with water, this being of importance for the manufacture of the papers. In accordance with this invention, it is also possible to produce indicators in the form of a powder which, in turn, can be further processed into shaped objects, such as tablets, rods, plugs, etc.

Among the reactive groups, the preferred groups are the 2(hydroxysulfonyloxy)-ethylsulfonyl group $HO-SO_2-O-CH_2-CH_2-SO_2-$ (designated hereinafter as the "HSS-group") and the N-methyl-N-[2-(hydroxysulfonyloxy)-ethyl]-sulfonamido group $HO-SO_2-O-CH_2CH_2-SO_2-N(CH_3)-$ (designated hereinbelow as the "N-methyl-HSS-amido group"). Additional reactive groups include, but are not limited to: monochlorotriazinyl, dichlorotriazinyl, mono-, di- and trichloropyrimidyl, dichloropyridazinyl, dichloroquinoxalinyl, dichlorophthalazinyl and 2-(hydroxy-sulfonyloxy)-ethylaminosulfonyl.

One or more, up to about 4, reactive groups can be present in the dyestuff molecule. In particular, dyes containing at most 2, and especially only one reactive group are preferred.

The azo dyes usable in accordance with this invention can contain one or more, particularly 1–4 sulfonic acid and/or carboxylic acid groups ($SO_3H$ or $COOH$). Preferred, however, are those dyes having a total of one or two $SO_3H$ groups and/or $COOH$ groups.

In addition to the reactive groups, the azo group and the $SO_3H$- and/or $COOH$-groups, the dyestuff molecules can contain further functional groups of a neutral, acidic or basic character, as they are conventional in azo dyes. One or more, approximately up to 5, preferably 1–3, of such additional substituents can be present, examples of same including, but not limited to: alkyl of 1–4 carbon atoms (preferably methyl or ethyl), OH, alkoxy of 1–4 carbon atoms (preferably methoxy or ethoxy), Cl, Br, $NO_2$, F, I, $CF_3$ or an amino group, optionally substituted by one or two alkyl groups of 1–4 carbon atoms each and/or by a phenyl or benzyl group (preferably amino, methylamino, dimethylamino, ethylamino, methylethylamino, diethylamino, phenylamino, benzylamino, N-methyl-N-benzylamino, or N-ethyl-N-benzylamino). In other words, the dyestuff has the formula $Ar-N=N-Ar$ wherein Ar, in both cases, is an aryl, preferably carbocyclic aryl residue forming with the azo group an organic azo dyestuff, with the provision that at least one aryl group is substituted by at least one reactive group and at least one aryl group is substituted by at least one radical selected from the group consisting of $-SO_3H$ and $-COOH$.

Of the above group, azo dyes of Formula I are especially useful:

$$R-N=N-R' \qquad \text{I}$$

wherein
R is phenyl or naphthyl substituted by at least one optionally substituted amino group or OH; and
R' is phenyl or naphthyl
and wherein at least one of R or R' is substituted by a 2-(hydroxysulfonyloxy)-ethylsulfonyl residue and/or by an N-methyl-N-[2-(hydroxysulfonyloxy)-ethyl]-sulfonamido residue, and wherein at least one of the residues R or R' is substituted by $-COOH$ and/or $SO_3H$, and wherein the residues R and R' are optionally substituted with groups conventional to organic azo dyestuffs and which, of course, do no deleteriously interfere with the function of either the reactive groups or the —COOH or —SO₃H radicals.

A preferred subgeneric group of azo dyes is of the Formula Ia:

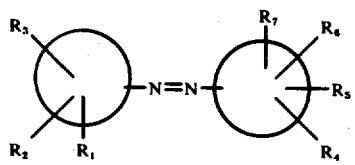
Ia wherein
the rings represent benzene or naphthalene rings;
one of the residues R₁ to R₇ is a 2-(hydroxysulfonyloxy)-ethylsulfonyl group or an N-methyl-N-[2-(hydroxysulfonyloxy)-ethyl]-sulfonamido group; another residue is a COOH- or SO₃H-group; one of the residues R₁ to R₃ represents an amino group optionally substituted by one or two alkyl groups of 1–4 carbon atoms respectively and/or a phenyl or benzyl group, or represents an OH-group; and the remaining residues R₁ to R₇ represent H, OH, alkyl of 1–4 carbon atoms or alkoxy of 1–4 carbon atoms, Cl, Br, NO₂ or SO₃H.

Especially preferred types of azo dyes are those of the Formulae Ib to Ii as follows:

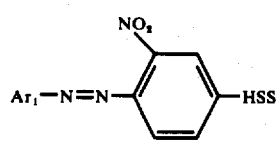
Ib wherein
Ar₁ represents 1- or 2-naphthyl substituted by an OH-group and one or two SO₃H-groups;

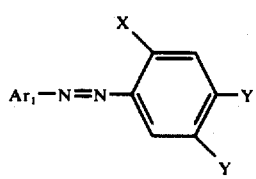
Ic wherein
X represents Cl or Br; and
one of the Y groups represents HSS and the other H;

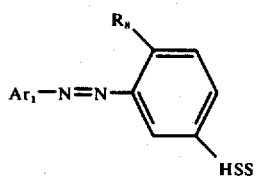
Id wherein
R₈ represents COOH or SO₃H;

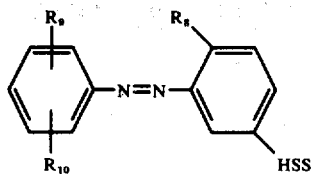
Ie wherein
R₉ represents methylamino, dimethylamino, ethylamino, diethylamino, anilino, N-methyl-N-benzylamino or N-ethyl-N-benzylamino; and
R₁₀ represents H, CH₃, COOH or SO₃H;

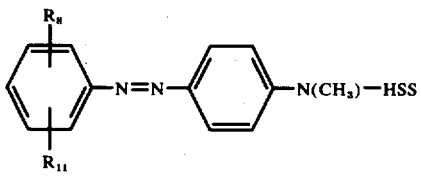
If wherein
R₁₁ represents methylamino, dimethylamino, ethylamino or diethylamino;

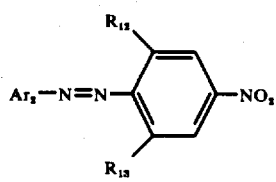
Ig wherein
Ar₂ represents a naphthyl residue substituted in the 1- or 2-position by an OH-group, and in the 6-position by an HSS- or N(—CH₃)-HSS-amido group, and optionally by an SO₃H-group;
R₁₂ is H or NO₂; and
R₁₃ is H or SO₃H;
but wherein at least one SO₃H-group must be contained;

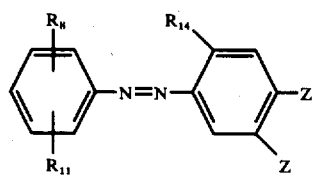
Ih wherein
R₁₄ represents H or OCH₃, and one of the Z groups represents HSS and the other H or CH₃;

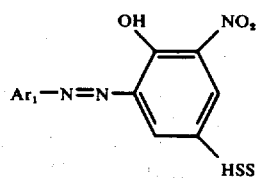
Ii

The azo dyes of the general Formula I can be produced in a conventional manner by diazotizing an amine of Formula II:

$H_2N-R'$    II wherein
R' has the above-indicated meanings,
and coupling the thus-obtained diazonium salt with a compound of Formula III:

R — H    III wherein
R has the above-indicated meanings.
Preferred amines are those of Formula IIa

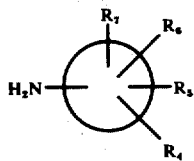

wherein
$R_4$–$R_7$ have the above-indicated meanings.
More specifically, examples of such amines to be converted into the diazo compound include, but are not limited to;
o-, m- and p-HSS-aniline; o-, m- and p-N-methyl-HSS-amido-aniline; 2-methoxy-4-HSS-aniline; 2-methoxy-4-HSS-5-methyl-aniline; 2-bromo-4-HSS-aniline; 2-chloro-4- and -5-HSS-aniline; 2-nitro-4- and -5-HSS-aniline; 2,6-dichloro-4-HSS-aniline; 2,6-dibromo-4-HSS-aniline; 2-hydroxy-3-nitro-5-HSS-aniline; o-, m- and p-nitroaniline; 2,4-dinitroaniline; 2,4-dinitroaniline-6-sulfonic acid; 5-HSS-aniline-2-sulfonic acid; 4-HSS-anthranilic acid; 1-amino-6-HSS-2-naphthol; 2-amino-6-HSS-1-naphthol-3-sulfonic acid; 5-HSS-naphthylamine.
Preferred coupling components are those of Formula IIIa

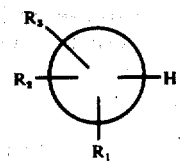

Examples of the above include, but are not limited to, the following compounds:
Methyl-,ethyl-, methylethyl-, dimethyl-, diethyl-, N-benzyl-N-methyl- and N-benzyl-N-ethylaniline; N-methyl- and N-ethyl-o-toluidine; diphenylamine; 2-, 3- and 4-methylamino-, -ethylamino-, dimethylamino- and -diethylaminobenzoic acid; 2-,3- and 4-nitro-, -methylamino-, ethylamino-, -dimethylamino- and -diethylaminobenzene-sulfonic acid; 1-naphthol; 1-naphthol -3- and -4-sulfonic acid; 1-naphthol-3,6- and -3,8-disulfonic acid; 6-N-methyl-HSS-amido-1-naphthol-3-sulfonic acid; 2-naphthol; 6-HSS-2-naphthol; 2-naphthol-6- and -7-sulfonic acid; and 2-naphthol-3,6- and -6,8-disulfonic acid.
The precedingly described starting materials can be synthesized by conventional processes such as those described in U.S. Pat. Nos. 3,135,779 and 3,197,456; many of them are known as such.
The diazotization and coupling processes are performed in a manner well known for the production of azo dyes. Thus, the amine can be suspended in water, mixed with the required excess amount of hydrochloric acid or sulfuric acid, and diazotized at temperatures of between −5° and +10° C by the addition of sodium nitrate under stirring. The thus-obtained diazonium salt can subsequently be reacted with the basic or acidic coupling component in an acidic or basic aqueous medium at temperatures of between −5° and 30° C, preferably under agitation.

The indicator papers of the present invention can be produced in several ways:
On the one hand, the paper can be colored during the manufacture thereof, by first suspending the paper raw material with water in suitable heaters, mixing the resultant suspension with an aqueous solution of the dye, and then asking the suspension alkaline by the addition of bases for fixing the dye on the fiber. After the reaction is terminated (about 30 minutes later), the fixing solution is removed by centrifuging, and then the dyed paper pulp is washed to neutral with desalinated water and further processed on a paper making machine in a conventional manner.
A second method involves imprinting finished paper with a dye solution and fixing the dyes by a brief immersion into a warm alkaline fixing solution at 60° C.
By still another technique, the dye solution can be applied to a paper previously made alkaline, which paper, after the application of the dye solution and a subsequent brief treatment in steam, is washed neutral and dried.
The thus-produced indicator papers do not bleed since the dyes are bound to the cellulose fiber. Furthermore, because these papers can remain in the solution-to-be-tested for a long period of time without any danger of bleeding, it is possible for the technician to take his time in order to conduct an exact comparison with the color scale, which is, of course, a prerequisite for a precise pH determination. These papers also permit the pH to be measured even in weakly or unbuffered solutions without encountering the difficulties associated with prior art indicators.
If a dye solution is employed containing two or more dyes coordinated to each other with respect to the change-over zones and boundary colors, then indicator papers are obtained covering a larger pH range.
An indicator paper containing several dyes can also be obtained by dyeing cellulose fibers separately with individual dyes and forming a sheet only from differently dyed cellulose fibers mixed in a specific proportion. The conventional mixed indicator papers cannot be produced according to this process because of the bleeding problem.
In addition to indicator papers, it is also possible to produce in an analogous manner powdery indicators. Such indicator powders can be added, for example, to a chemical reaction solution wherein the pH curve is to be followed during the reaction; after termination of the reaction, the powder can be separated from the solution simply by filtration. The resultant solution is thereby not contaminated. Accordingly, the constancy of the pH value, important in a large number of chemical or biochemical reactions, can be readily controlled visually with the aid of the indicator powders of the present invention.
Such indicator powders can also be employed in place of conventional liquid indicators during titrations and, if desired, the powder can be filtered off after the titration end-point has been reached.
Cellulose, in particular microcrystalline cellulose, is firmly established as an adsorbent in column and thinlayer chromatography. If substances to be separated thereby differ in their pH values, or are eluted at different pH values, then it is advantageous to employ a cellulose dyed with the reactive indicator dyestuff of this invention, either by itself, in a mixture with ordinary cellulose powder, or even as a combination of several layers changing over at different pH values. In this manner, the boundary of the desired zone can be visually determined, facilitating further separation. The same principle can also be employed in connection with paper chromatography.

The indicator powders, after slight moistening, can also be strewn on solid objects for pH measurement and the like. After drying, the object can be cleaned without leaving any traces by simply brushing it off.

In many cases where it is desired to determine, without contamination, the pH value, the redox potential, the hardness or other characteristic values of liquids or solids, it is advantageous to employ shaped bodies of cellulose or cellulose derivatives dyed with reactive indicator dyestuffs. In this connection, it is of no importance whether preformed shaped bodies are dyed subsequently or whether dyed cellulose powders or fibers are shaped, if desired with the additon of a binder.

Thus, it is possible to determine, without leaving any trace, the pH of documents, books or artifacts (e.g. paintings) in order to determine preservation measures, by using a rod, plug or film, etc. made of cellulose dyed with an indicator dyestuff according to this invention, and optionally containing additionally a moistening agent.

In a similar manner, foodstuffs can be examined without any contamination; for example, foodstuffs can be tested to determine the presence of acidic preservation, and fats can be examined with regard to the formation of fatty acids.

Cellulose powders, papers or shaped objects dyed with reactive indicator dyestuffs of this invention can be employed to indicate the pH of flowing media. Thus, for example, one or more zones can be provided with an inspection glass for observing varying pH values by virtue of indicator placed in the stream, a technique helpful for monitoring continuous processes, e.g. a waste water or conversion process. In case of a reaction wherein it is important to maintain a constant pH, or wherein the terminal reaction is significant, it is also possible to continuously branch off a partial amount of a side stream and then recycle same to the process. In the same way, an indicator zone can also be inserted after employing an absorption agent or an exchanger, in order to indicate the degree of saturation or exhaustion. Furthermore, it is possible to pass a gaseous stream, for example, an air stream, through such a filter produced from an indicator powder of this invention, and thus determine the presence of acidic or basic components.

A well-proven and therefore very popular method for the corrosion-protection of iron containers holding liquid combustibles or fuels containing entrained water is the addition of salts of nitrous acid in the presence of soda. However, the corrosion protection is effective only as long as an at least weakly alkaline ambient medium is maintained. Such it is impossible to control the pH of the water accumulated on the tank bottom by means of conventional indicator papers, due to the washing-out effect, there exists an uncertainty,, and attempts are made to eliminate such uncertainty by a frequent, but in most cases, unnecessary addition of fresh corrosion protection salt. By means of the indicator papers or shaped bodies of the present invention, attached in a suitable manner to the gauge rod employed for measuring the level of the contents, it is possible to conduct a precise measurement of the alkalinity of the water, thereby eliminating the former wasteful technique.

Lime (calcium hydroxide) and cement react alkaline as long as they have not completely been set by $CO_2$ absorption. Since many coats of paint are sensitive to alkalies, it is advantageous to determine the pH of the mortar or plaster before such paints are applied. This can be accomplished with the aid of the indicator papers, films or shaped bodies of this invention — thereby avoiding the presence of any colored test spots on material to be painted.

Further applications will occur to those of ordinary skill, for example: the condition of photographic baths; measuring or monitoring the pH of aquariums, waste waters, swimming pools; body fluids; industrial processes, e.g. in dairies, and fermentation processes, for example, in the production of cheese, beer or wine; in the galenical or cosmetic arts; and in paper manufacture. Furthermore, the pH value can be detrmined on the surface of solids, such as, for example, textiles, woods, metals or synthetic materials.

Aside from cellulose as a carrier material, other conventional materials can be used, such as any insoluble polymeric material having free hydroxyl and/or NH groups, including cellulose ethers and esters (as long as there are still free OH groups present), polyamides, wool, and silk; cellulose including not only paper but any native or regenerated form of cellulose as cotton, linen, rayon.

Without further elaboration, it is believed that one skilled in the art can, using the preceding description, utilize the present invention to its fullest extent. The following preferred specific embodiments are, therefore, to be construed as merely illustrative, and not limitative, of the remainder of the disclosure in any way whatsoever.

EXAMPLE 1 a. Under agitation, 97.6 g. of 4-(2-hydroxysulfonyloxy-ethylsulfonyl)-2-aminobenzoic acid (4-HSS-2-aminobenzoic acid) are suspended in 550 ml of water and mixed, at about 10° C, with 120 g. of 50% sulfuric acid. Thereafter, with further agitation, a solution of 20 g of sodium nitrite in 150 ml of water is added dropwise, within a period of about 30 minutes, to the reaction solution at 0°–5° C, and the stirring is then continued for one hour at the same temperature. The resultant crystalline internal diazonium salt is then vacuum-filtered.

In order to convert the diazonium salt into the reactive dyestuff, the salt (about 94g.) is suspended in 450 ml of water, mixed, at 5° C, with a solution of 47.3 g. of diphenylamine in 240 ml of acetic acid, and stirred at first for 1 hour at 5° C, and thereafter for another hour at 20° C. The thus-obtained dark green 4-anilino-3'-(2-hydroxysulfonyloxy-ethylsulfonyl)-azobenzene-6'-carboxylic acid (4-anilino-3'-HSS-azobenzene-6'-carboxylic acid; designated below as "Dyestuff No. 1") is vacuum-filtered, washed with 100 ml of 2N acetic acid, and dried at 35° C under reduced pressure. Yield: about 80% theory. Absorption spectrum: $\lambda_{max}$430 m$\mu$ (in $CH_3OH$).

The starting material 4-(2-hydroxysulfonyloxy-ethyl-sulfonyl)-2-aminobenzoic acid is produced for example, by acetylation of 4-sulfo-anthranilic acid, chlorination to give 2-acetamido-4-chlorosulfonylbenzoic acid, subsequent reactions with sodium bisulfite, 2-chloroethanol, and sulfuric acid, and hydrolysis.

B. Indicator Film 0.5 g. of transparent paper (e.g., cellophane MSAT 450**) are immersed in 25 ml of a 1% methanolic solution of the dyestuff. After 5 minutes, the solution is made alkaline with 5 ml of 2N NaOH and, after another 15 minutes, the paper is washed neutral with water. The transparent film having a high wet fastness changes over in the pH range of 0 – 4.5.

** MSAT 450 is a short designations by the supplier (Kalle & Co., Wiesbaden, Germany) standing for "Moistureproof Sealing Anchored Transparent of a thickness of 45 micron."

c. Indicator Paper 0.02 g. of the dyestuff converted into the Na-salt are dissolved in 125 ml of water to form a clear solution. This solution is then mixed successively with 2.5 g. of the paper to be dyed, 20 g. of sodium chloride, 2.5 g. of sodium carbonate, and 2.6 ml of 2N sodium hydroxide solution, and allowed to stand for 30 minutes at room temperature. Then, the dyed paper is washed neutral and a sheet is produced on a sheet making machine. The indicator paper manufactured in this manner, which has an excellent wet proofness, changes from deep purple to dark orange between the pH values of 0 and 4.5. Of the employed dyestuff, 60% is attached to the paper.

In a similar manner, indicator papers having the same excellent fastness are obtained with the dyestuffs set forth in the table below:

| No. | Dyestuff (the parenthetical expression denotes the $\lambda_{max}$ in water at a pH of 7, unless differently indicated) | Change-Over Range | Change-Over Colors of the Paper |
|---|---|---|---|
| 1 | 4-Anilino-3'-HSS-azobenzene-6'-carboxylic acid (435 mμ at pH 6) | 0 – 4.5 | deep purple - dark orange |
| 2 | 6-Dimethylamino-3' HSS-azobenzene-2-carboxylic acid | deep red- 4.0 – 6.5 | orange |
| 3 | 4-Ethylamino-3'-HSS-azobenzene-5-sulfonic acid | 0 – 2.5 | light red - yellow |
| 4 | 1-(p-HSS-phenylazo)-2-naphthol-6,8-disulfonic acid | 11.0 – 13.0 | yellow - brownish violet |
| 5 | 6-Dimethylamino-4'-HSS-azobenzene-2-sulfonic acid | 1.0 – 3.0 | red - orangish yellow |
| 6 | 4-Ethylamino-4'-HSS-azobenzene-5-carboxylic acid | 1.0 – 2.5 | red - orange |
| 7 | 4-Ethylamino-4'-HSS-azobenzene-5-sulfonic acid | 0 – 4.0 | red - yellow |
| 8 | 6-Dimethylamino-4'-HSS-6'-methoxy-azobenzene-2-carboxylic acid | 4.5 – 7.5 | bluish violet - red |
| 9 | 4-Methylamino-4'-HSS-6'-methoxy-azobenzene-5-sulfonic acid | 0.5 – 2.5 | red - yellow |
| 10 | 2-(2-sulfo-5-HSS-phenylazo)-1-naphthol-3,6-disulfonic acid | 6.0 – 8.0 | yellow - red |
| 11 | 2-(2-sulfo-5-HSS-phenylazo)-1-naphthol-3-sulfonic acid | 9.5 – 12.0 | yellow - red |
| 12 | 1-(2-sulfo-5-HSS-phenylazo)-2-naphthol-3,6-disulfonic acid | 11.0 – 12.5 | orange - red |
| 13 | 1-(2-sulfo-5-HSS-phenylazo)-2-naphthol-7-sulfonic acid | 11.0 – 12.5 | orange - red |
| 14 | 6-Dimethylamino-3'-HSS-azobenzene-2,6'-disulfonic acid | 0.5 – 2.0 | red - orange |
| 15 | 4-Ethylamino-3'-HSS-azobenzene-5,5'-disulfonic acid | 3.5 – 5.0 | red - yellowish orange |
| 16 | 6-Dimethylamino-3'-methyl-4'-HSS-6'-methoxy-azobenzene-2-carboxylic acid | 4.5 – 6.5 | violet - red |
| 17 | 4-Ethylamino-3'-methyl-4'-HSS-6'-methoxy-azobenzene-5-sulfonic acid | 1.0 – 2.5 | violet - orange |
| 18 | 4-Methylamino-3'-methyl-4'-HSS-6'-methoxy-azobenzene-5-sulfonic acid | 0 – 2.5 | violet - orange |
| 19 | 1-(2-Bromo-4-HSS-phenylazo)-2-naphthol-3,6-disulfonic acid | 9.5 – 12.0 | orange - violet |
| 20 | 1-(2-Bromo-4-HSS-phenylazo)-2-naphthol-6,8-disulfonic acid | 11.0 – 13.0 | yellowish orange - brownish violet |
| 21 | 1-(2-Bromo-4-HSS-phenylazo)-2-naphthol-6-sulfonic acid | 11.0 – 13.0 | orangish red - violet |
| 22 | 6-Dimethylamino-3'-HSS-azobenzene-2,6'-dicarboxylic acid | 4.5 – 6.5 | red - orange |
| 23 | 2-Sulfo-6-dimethylamino-3'-HSS-azobenzene-6'-carboxylic acid | 4.0 – 6.5 | red - yellow |
| 24 | 4-Ethylamino-3'-HSS-azobenzene-5,6'-dicarboxylic acid | 5.5 – 7.5 | red - rellowish orange |
| 25 | 4-Methylamino-5-sulfo-3'-HSS-azobenzene-6'-carboxylic acid | 2.5 – 4.5 | light red - yellow |
| 26 | 4-Methylamino-3'-HSS-azobenzene-5,6'-dicarboxylic acid | 5.0 – 7.0 | deep red - orange |
| 27 | 4-Dimethylamino-3'-HSS-azobenzene-6'-carboxylic acid | 4.5 – 6.0 | red - yellow |
| 28 | 4-Methylamino-3'-HSS-azobenzene-6'-carboxylic acid | 3.5 – 6.5 | red - yellow |
| 29 | 4-Ethylamino-5-methyl-3'-HSS-azobenzene-6'-carboxylic acid | 4.0 – 7.0 | red - yellow |

-continued

| No. | Dyestuff (the parenthetical expression denotes the $\lambda_{max}$ in water at a pH of 7, unless differently indicated) | Change-Over Range | Change-Over Colors of the Paper |
|---|---|---|---|
| 30 | 4-Diethylamino-3'-HSS-azobenzene-6'-carboxylic acid | 5.0 – 6.5 | reddish violet - yellowish orange |
| 31 | 1-(2-Nitro-4-HSS-phenylazo)-2-naphthol-3,6-disulfonic acid | 11.5 – 12.5 | pale orange - violet |
| 32 | 2-(2-Nitro-4-HSS-phenylazo)-1-naphthol-4-sulfonic acid | 8.0 – 10.0 | reddish orange - violet |
| 33 | 1-(2-Nitro-4-HSS-phenylazo)-2-naphthol-6-sulfonic acid | 11.0 – 13.5 | orange - violet |
| 34 | 1-(2-HSS-phenylazo)-2-naphthol-3,6-disulfonic acid | 9.5 – 12.0 | orange - red |
| 35 | 1-(2,6-Dibromo-4-HSS-phenylazo)-2-naphthol-3,6-disulfonic acid | 10.0 – 12.0 | reddish orange - red |
| 36 | 4-Methylamino-4'-(N-methyl-HSS-amido)-azobenzene-5-carboxylic acid | 0 – 2.0 | violet - yellow |
| 37 | 4-Ethylamino-4'-(N-methyl-HSS-amido)-azobenzene-5-sulfonic acid | 0 – 2.0 | violet - light brown |
| 38 | 1-(2-Chloro-5-HSS-phenylazo)-2-naphthol-3,6-disulfonic acid (485 m$\mu$) | 9.0 – 12.5 | orange - red |
| 39 | 1-(2-Chloro-5-HSS-phenylazo)-2-naphthol-6-sulfonic acid | 11.0 – 12.5 | orangish red - red |
| 40 | 2-(2-Hydroxy-3-nitro-5-HSS-phenylaxo)-1-naphthol-3,8-disulfonic acid | 1.0 – 3.5 | orangish red - violet |
| 41 | 2-(2-Hydroxy-3-nitro-5-HSS-phenylazo)-1-naphthol-3-sulfonic acid | 1.0 – 3.0 | reddish orange - violet |
| 42 | 1-(2-Hydroxy-3-nitro-5-HSS-phenylazo)-2-naphthol-7-sulfonic acid | 1.0 – 2.5 | red - violet |
| 43 | 2-(2-Sulfo-4-nitrophenylazo)-6-HSS-1-naphthol-3-sulfonic acid | 11.0 – 13.0 | yellow - violet |
| 44 | 2-(2-Hydroxy-6-HSS-1-naphthylazo)-5-nitrobenzenesulfonic acid | 8.0 – 10.0 | brown - brownish violet |
| 45 | 4-Methylamino-4'-(N-methyl-HSS-amido)-azobenzene-5-sulfonic acid (405 m$\mu$) | 0 – 3.0 | purplish red - light yellow |
| 46 | 4-(N-Benzyl-N-ethylamino)-3'-HSS-azobenzene-6'-carboxylic acid (455 m$\mu$ at pH 8) | 3.5 – 7.0 | purplish red - yellowish orange |
| 47 | 2-(2-Sulfo-4,6-dinitrophenylazo)-6-(N-methyl-HSS-amido)-1-naphthol-3-sulfonic acid (455 m$\mu$ at pH 3) | 4.0 – 6.5 | yellowish orange - deep green |
| 48 | 2-(2,4-dinitrophenylazo)-6-(N-methyl-HSS-amido)-1-naphthol-3-sulfonic acid (465 m$\mu$ at pH 3) | 4.0 – 7.5 | orangish yellow - deep blue |
| 49 | 2-(2-Nitro-4-HSS-phenylazo)-1-naphthol-3,6-disulfonic acid (458 m$\mu$ at pH 4) | 5.0 – 8.0 | yellowish orange - violet-brown |
| 50 | 4-Anilino-3'-HSS-azobenzene-6'-sulfonic acid (447 m$\mu$) | 0 – 3.0 | deep purple - yellowish orange |
| 51 | 2-(2-Nitro-4-HSS-phenylazo)-1-naphthol-3-sulfonic acid | 5.5 – 9.0 | orange - dark brown |
| 52 | 2-(4-Hydroxynaphthyl-1-azo)-4-HSS-benzenesulfonic acid (455 m$\mu$) | 8.0 – 10.5 | yellowish orange - deep red |
| 53 | 4-(N-Methyl-HSS-amido)-2'-dimethylamino-azobenzene-6'-sulfonic acid (435 m$\mu$) | 1.0 – 4.0 | purple - yellow |
| 54 | 1-(2-Nitro-4-HSS-phenylazo)-2-naphthol-7-sulfonic acid (485 m$\mu$) | 11.0 – 13.5 | reddish orange - reddish violet |
| 55 | (1-(2-Nitro-4-HSS-phenylazo)-2-naphthol-6,8-disulfonic acid (485 m$\mu$) | 12.5 – 14.0 | reddish orange - dark brown |
| 56 | 2-(2-Hydroxy-6-HSS-1-naphthylazo)-3,5-dinitrobenzenesulfonic acid (465 m$\mu$) | 8.0 – 10.5 | orangish yellow - violet |
| 57 | 4-(N-Methyl-HSS-amido)-2'-dimethylamino-azobenzene-6'-carboxylic acid (455 m$\mu$ at pH 8) | 3.5 – 6.0 | red - yellowish orange |

The dyestuffs mentioned in the table can be made by diazotizing the corresponding amines and coupling the thus obtained diazonium salts with the corresponding coupling components, as outlined above. Furthermore, they can be prepared by esterification of the corresponding compounds carrying an HO—CH$_2$—CH$_2$—SO$_2$—group instead of a HSS group with sulfuric acid.

EXAMPLE 2

Under the conditions set forth in Example 1(c), and with an aqueous dyestuff solution containing the dyestuffs 38, 52, 54 and 55 in a ratio of 2.5 : 1 : 5 : 5, a wet-proof indicator paper is obtained which changes over from yellow over red to deep violet and the change-over zone ranges between pH 9 and 14.

EXAMPLE 3

A paper dyed with dyestuff 49 in accordance with Example 1(c) is blended with a second paper, dyed under the same conditions with dyestuff 52, in a ratio 1 : 1. The indicator paper produced from this cellulose fiber mixture changes over in the range of pH 5.5–10.0 from orange-yellow to violet.

EXAMPLE 4

A 0.5% aqueous solution containing the reactive indicator dyes No. 1 and No. 53 in a proportion of 1 : 3 is applied by the intaglio printing method to finished paper in the form of a longitudinally extending indicator strip. Simultaneously and directly adjoining this strip, a further strip is applied with the aid of a second 0.5% dyestuff solution containing the reactive indicator dyestuffs 49, 51 and 52 in a proportion of 1.4 : 1 : 2.6. The paper, impregnated in this manner, is immersed for 1 minute into a warm fixing solution of 80° C containing 20% sodium chloride, 2.5% sodium carbonate and 0.07% sodium hydroxide. After fixing of the dyestuffs, the paper is washed neutral and dried. By means of the thus-produced indicator paper, pH values in the range from 0 to 10 can be accurately measured, since the dyestuffs are joined to the fiber in such a manner that they cannot be washed out. The indicator zones disposed side-by-side effect a color contrast with respect to the other strip, which is advantageous for read-off accuracy.

EXAMPLE 5

A paper having the properties described in Example 4 can also be obtained by first making the paper to be dyed alkaline by immersion into the alkaline fixing solution, then applying the dyestuff solutions mentioned in Example 4 in the same way, and thereafter conducting the bonding of the dyes with the fiber, by treating the impregnated paper for one minute with steam.

Dyestuff combinations employed in accordance with the invention, for example, according to Examples 2 to 5, comprise preferably at least two of the above-mentioned azo dyes No. 1, 38, 45, 46, 47, 48, 49, 50, 51, 52, 53, 54, 55, 56 and 57. In general, at most 4 of the above-mentioned dyes are employed in these combinations. The dyestuff combinations set out below have proven to be especially useful:

| pH Range | Dyes No. | Mixture Ratio (Weight Basis) | Boundary Colors |
|---|---|---|---|
| 0 – 7 | 1 + 47 + 53 | 1 : 1 : 3 | violet - yellow - green |
|  | 1 + 48 30 53 | 1 : 1 : 3 | violet - yellow - blue |
|  | 1 + 50 | 4 : 1 | violet - yellow |
|  | 1 + 45 | 1 : 2.5 | violet - yellow |
|  | 1 + 53 | 1 : 3 | violet - yellow |
| 4 – 10 | 48 + 49 + 52 | 2 : 2 : 1 | yellow - green - violet |
|  | 49 + 51 + 52 | 1.4 : 1 : 2.6 | yellow - brown - red-violet |
|  | 49 + 51 + 56 | 2 : 1 : 1 | yellow - brown - violet |
|  | 47 + 52 | 1 : 1 | yellow - deep red |
|  | 49 + 52 | 1 : 1 | yellow - deep red |
|  | 51 + 52 | 1 : 1 | yellow - deep red |
| 9 – 14 | 38 + 52 + 54 + 55 | 2.5 : 1 : 5:5 | yellow - red - violet |
|  | 54 + 55 + 56 | 1 : 0.5 : 2 | yellow - red - violet |
|  | 38 + 54 | 1 : 1 | red-orange - red-lilac |
|  | 38 + 55 | 1 : 1 | red-orange - dark brown |

In the following example, there is described a large scale production of an indicator paper of this invention:

EXAMPLE 6

In 800 liters of fully desalted water, 0.160 kg of the dye 2-(4-hydroxynaphthyl-1-azo)-4-HSS-benzenesulfonic acid (dyestuff No. 52) is dissolved. Then, 40 kg of linters are introduced into the dyestuff solution and beaten under vigorous stirring, resulting in a thick, yellow paper pulp. Thereafter, in intervals of 5 minutes, 40 kg of sodium chloride, 20 kg of sodium carbonate and 4.16 liters of 32% sodium hydroxide solution are admixed to this paper pulp. In order to fix the dyestuff to the cellulose fiber, the mixture is allowed to stand for another 30 minutes at room temperature.

After the reaction is terminated, the thus-dyed paper pulp is pumped into a centrifugal separator. After the fixing solution has been removed by centrifugal force, the paper mass is washed neutral with 2,000 liters of desalinated water on the running centrifugal separator. Subsequently, the most centrifuged product is ground for 40 minutes in a hollander machine and then processed directly from the vat onto a cylinder paper machine, thereby forming the finished indicator paper. 80% of the dyestuff employed is firmly attached to the paper.

EXAMPLE 7

Dyes usable in accordance with the invention with nitrogen-containing heterocyclic reactive groups which can be manufactured by diazotiazation of the basic amines and coupling include, but are not limited to, the following:

2-(2,4-Dinitrophenylazo)-6-(4,6-dichloro-1,3,5-triazinyl-2-amino)-1-naphthol-3-sulfonic acid;

2-(2,4-Dinitrophenylazo)-6-(2,6-dichloro-pyrimidyl-4-amino)-1-naphthol-3-sulfonic acid;

2-(p-Sulfophenylazo)-6-(4,6-dichloro-1,3,5-triazinyl-2-amino)-1-naphthol-3-sulfonic acid;

2-(p-Sulfophenylazo)-6-(2,6-dichloro-pyrimidyl-4-amino)-1-naphthol-3-sulfonic acid;

2-(3-Sulfo-4-dimethylamino-phenylazo)-4-(4-amino-6-chloro-1,3,5-triazinyl-2-amino)-benzenesulfonic acid;

2-(3-Sulfo-4-dimethylamino-phenylazo)-4-(2,6-dichloro-pyrimidyl-4-amino)-benzenesulfonic acid;

2-(2-Hydroxy-3,6-disulfo-1-naphthylazo)-4-(4-amino-6-chloro-1,3,5-triazinyl-2-amino)-benzene-sulfonic acid;

2-(2-Hydroxy-3,6,-disulfo-1-naphthylazo)-4-(2,6-dichloro-pyrimidyl-4-amino)-benzenesulfonic acid;

1-(2-Hydroxy-4-sulfo-6-nitro-1-naphthylazo)-4-(4-amino-6-chloro-1,3,5-triazinyl-2-amino)-benzene; and 1-(2-Hydroxy-4-sulfo-6-nitro-1-naphthylazo)-4-(2,6-dichloro-pyrimidyl-4-amino)-benzene.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for determining the pH of a media, which comprises (a) contacting said media with a non-bleeding pH indicator comprising an insoluble polymer carrier having free hydroxyl or NH groups or mixtures thereof, and bound to said carrier an organic azo dyestuff capable of changing color in response to a change in pH, said dye being of the formula Ar — N = N — Ar wherein Ar is an aryl forming with the azo group said organic azo dyestuff, with the provision that at least one aryl group is substituted by at least one reactive group capable of forming a chemical bond with said polymeric carrier, and at least one aryl group is substituted by at least one other radical selected from the group consisting of —$SO_3H$ and —COOH, said reactive group being 2-(hydroxysulfonyloxy)-ethylsulfonyl, N-methyl-N-[2-(hydroxysulfonyloxy)-ethyl]-sulfonamide, monochlorotriazinyl, dichlorotriazinyl, mono-, di- and trichloropyrimidyl, dichloropyridazinyl, dichloroquinoxalinyl, dichlorophthalazinyl or 2-(hydroxysulfonyloxy)-ethylamino-sulfonyl; and (b) determining the pH from the resultant color of said indicator.

2. A process as defined by claim 1 wherein said reactive group is 2-hydroxysulfonyloxy-ethylsulfonyl or N-methyl-N-(2-hydroxysulfonyloxy-ethylsulfonyl)-amido.

3. A process as defined by claim 1 wherein said organic azo dyestuff comprises a member selected from the group consisting of 4-anilino-3'-(2-hydroxysulfonyloxy-ethylsulfonyl)-azobenzene-6'-carboxylic acid, 1-[2-chloro-5-(2-hydroxysulfonyloxy-ethylsulfonyl)-phenylazo]-2-naphthol-3,6-disulfonic acid, 4-methylamino-4'-[N-methyl-N-(2-hydroxysulfonyloxy-ethylsulfonyl)-amido]-azobenzene-5-sulfonic acid, 4-(N-benzyl-N-ethylamino)-3'-(2-hydroxysulfonyloxy-ethylsulfonyl)-azobenzene-6'-carboxylic acid, 2-(2-sulfo-4,6-dinitrophenylazo)-6-[N-methyl-N-(2-hydroxysulfonyloxy-ethylsulfonyl)-amido]-1-naphthol-3-sulfonic acid, 2-(2,4-dinitrophenylazo)-6-[N-methyl-N-(2-hydroxysulfonyloxy-ethylsulfonyl)-amido]-1-naphthol-3-sulfonic acid, 2-[2-nitro-4-(2-hydroxysulfonyloxy-ethylsulfonyl)-phenylazo]-1-naphthol-3,6-disulfonic acid, 4-anilino-3'-(2-hydroxysulfonyloxy-ethylsulfonyl)-azobenzene-6'-sulfonic acid, 2-[2-nitro-4-(2-hydroxysulfonyloxy-ethylsulfonyl)-phenylazo]-1-naphthol-3-sulfonic acid, 2-(4-hydroxynaphthyl-1-azo)-4-(2-hydroxysulfonyloxy-ethylsulfonyl)-benzenesulfonic acid, 4-[N-methyl-N-(2-hydroxysulfonyloxy-ethylsulfonyl)-amido]-2'-dimethylamino-azobenzene-6'-sulfonic acid, 1-[2-nitro-4-(2-hydroxysulfonyloxy-ethylsulfonyl)-phenylazo]-2-napthol-7-sulfonic acid, 1-[2-nitro-4-(2-hydroxysulfonyloxy-ethylsulfonyl)-phenylazo]-2-naphthol-6,8-disulfonic acid, 2-[2-hydroxy-6-(2-hydroxysulfonyloxy-ethylsulfonyl)-1-naphthylazo]-3,5-dinitrobenzene-sulfonic acid and 4-[N-methyl-N-(2-hydroxysulfonyloxy-ethylsulfonyl)-amido]-2'-dimethylamino-azobenzene-6'-carboxylic acid.

4. A process as defined by claim 1 wherein said indicator is in the form of a substantially inflexible shaped object.

5. A process as defined by claim 1 wherein said dyestuff is of the formula

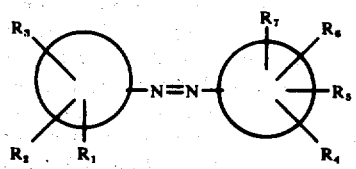

Ia wherein
the rings represent benzene or naphthalene rings;
one of the residues $R_1$ to $R_7$ is a 2-(hydroxysulfonyloxy)-ethylsulfonyl group or an N-methyl-N-[2-(hydroxysulfonyloxy)-ethyl]-sulfonamido group; another residue is a COOH- or $SO_3H$-group; one of the residues $R_1$ to $R_3$ represents an amino group optionally substituted by one or two alkyl groups of 1–4 carbon atoms respectively and/or a phenyl or benzyl group, or represents an OH-group; and the remaining residues $R_1$ to $R_7$ represent H, OH, alkyl of 1–4 carbon atoms or alkoxy of 1–4 carbon atoms, Cl, Br, $NO_2$ or $SO_3H$.

6. A process as defined by claim 1 wherein said dyestuff is of the formula

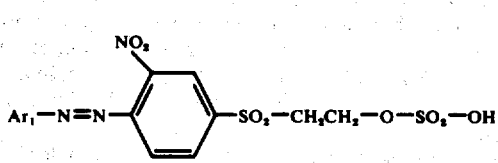

Ib wherein
$Ar_1$ represents 1- or 2-naphthyl substituted by an OH-group and one or two $SO_3H$-groups.

7. A process as defined by claim 1 wherein said dyestuff is of the formula

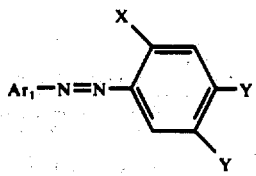

Ic wherein
$Ar_1$ represents 1- or 2-naphthyl substituted by an OH-group and one or two $SO_3H$-groups;
X represents $NO_2$Cl or Br; and one of the Y groups represents —SO$_2$—CH$_2$CH$_2$—O—SO$_2$OH and the other H.

8. A process as defined by claim 1 wherein said dyestuff is of the formula

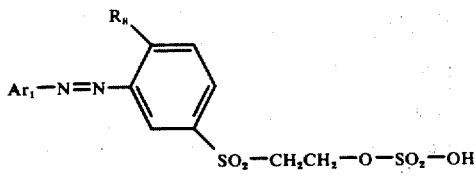

Id wherein
Ar$_1$ represents 1- or 2-naphthyl substituted by an OH-group and one or two SO$_3$H-groups; and
R$_8$ represents COOH or SO$_3$H.

9. A process as defined by claim 1 wherein said dyestuff is of the formula

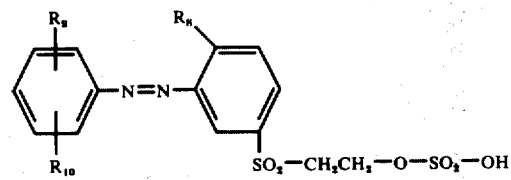

Ie wherein
R$_8$ represents COOH or SO$_3$H;
R$_9$ represents methylamino, dimethylamino, ethylamino, diethylamino, anilino, N-methyl-N-benzylamino or N-ethyl-N-benzylamino; and
R$_{10}$ represents H, CH$_3$, COOH or SO$_3$H.

10. A process as defined by claim 1 wherein said dyestuff is of the formula

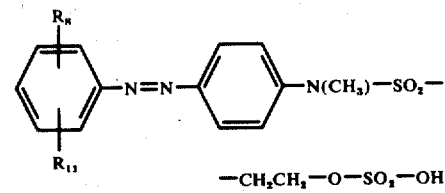

If wherein
R$_8$ represents COOH or SO$_3$H; and
R$_{11}$ represents methylamino, dimethylamino, ethylamino or diethylamino.

11. A process as defined by claim 1 wherein said dyestuff is of the formula

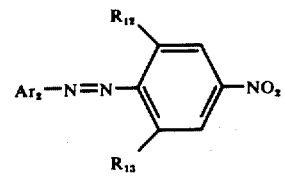

Ig wherein
Ar$_2$ represents a naphthyl residue substituted in the 1- or 2-position by an OH-group, and in the 6-position by an HO—SO$_2$—CH$_2$CH$_2$—SO$_2$— or HO—SO$_2$—O—CH$_2$CH$_2$—SO$_2$—N(CH$_3$)—, and optionally by an SO$_3$H-group;

R$_{12}$ is H or NO ; and
R$_{13}$ is H or SO$_3$H;
but wherein at least one SO$_3$H-group must be contained.

12. A process as defined by claim 1 wherein said dyestuff is of the formula

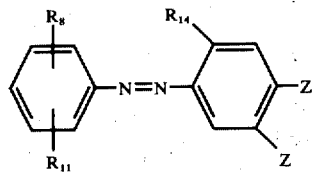

Ih wherein
R$_8$ represents COOH or SO$_3$H;
R$_{11}$ represents methylamino, dimethylamino, ethylamino or diethylamino, and
R$_{14}$ represents H or OCH$_3$, and one of the Z groups represents HO—SO$_2$—O—CH$_2$CH$_2$—SO$_2$—, and the other H or CH$_3$.

13. A process as defined by claim 1 wherein said dyestuff is of the formula

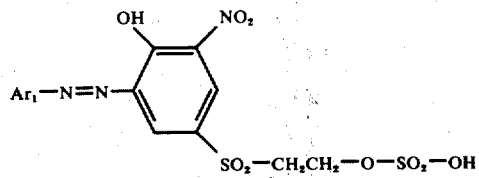

Ii wherein
Ar$_1$ represents 1- or 2-naphthyl substituted by an OH-group and one or two SO$_3$H-groups.

14. A process as defined by claim 1, said dyestuff being selected from the group consisting of
4-anilino-3'-(2-hydroxysulfonyloxy-ethylsulfonyl)-azobenzene-6'-carboxylic acid;
6-dimethylamino-3'-(2-hydroxysulfonyloxy-ethylsulfonyl)-azobenzene-2-carboxylic acid;
4-ethylamino-4'-(2-hydroxysulfonyloxy-ethylsulfonyl)-azobenzene-5-carboxylic acid;
6-dimethylamino-4'-(2-hydroxysulfonyloxy-ethylsulfonyl)-6'-methoxy-azobenzene-2-carboxylic acid;
6-dimethylamino-3'-methyl-4'-(2-hydroxysulfonyl-ethylsulfonyl)-6'-methoxy-azobenzene-2-carboxylic acid;
6-dimethylamino-3'-(2-hydroxysulfonyloxy-ethylsulfonyl)-azobenzene-2,6'-dicarboxylic acid;
2-sulfo-6-dimethylamino-3'-(2-hydroxysulfonyloxy-ethylsulfonyl)-azobenzene-6'-carboxylic acid;
4-ethylamino-3'-(2-hydroxysulfonyloxy-ethylsulfonyl)-azobenzene-5,6'-dicarboxylic acid;
4-methylamino-5-sulfo-3'-(2-hydroxysulfonyloxy-ethylsulfonyl)-azobenzene-6'-carboxylic acid;
4-methylamino-3'-(2-hydroxysulfonyloxy-ethylsulfonyl)-azobenzene-5,6'-dicarboxylic acid,
4-dimethylamino-3'-(2-hydroxysulfonyloxy-ethylsulfonyl)-azobenzene-6'-carboxylic acid;
4-methylamino-3'-(2-hydroxysulfonyloxy-ethylsulfonyl)-azobenzene-6'-carboxylic acid;
4-ethylamino-5-methyl-3'-(2-hydroxysulfonyloxy-ethylsulfonyl)-azobenzene-6'-carboxylic acid;
4-diethylamino-3'-(2-hydroxysulfonyloxy-ethylsulfonyl)-azobenzene-6'-carboxylic acid;

4-methylamino-4'-[N-methyl-N-(2-hydroxysulfonyloxy-ethylsulfonyl) -amido]-azobenzene-5-carboxylic acid;

4-(N-benzyl)-N-ethylamino)-3'-(2-hydroxysulfonyloxy-ethylsulfonyl)-azobenzene-6'-carboxylic acid; and 4-[N-methyl-N-(2-hydroxysulfonyloxy-ethylsulfonyl)-amido]-2'-dimethylamino-azobenzene-6'-carboxylic acid.

15. A process as defined by claim 1, said dyestuff being selected from the group consisting of 4-ethylamino-3'-(2-hydroxysulfonyloxy-ethylsulfonyl)-azobenzene-5-sulfonic acid;

6-dimethylamino-4'-(2-hydroxysulfonyloxy-ethylsulfonyl)-azobenzene-2-sulfonic acid;

4-ethylamino-4'-(2-hydroxysulfonyloxy-ethylsulfonyl)-azobenzene-5-sulfonic acid;

4-methylamino-4'-(2-hydroxysulfonyloxy-ethylsulfonyl)-6'-methoxy-azobenzene-5-sulfonic acid;

2-[2-sulfo-5-(2-hydroxysulfonyloxy-ethylsulfonyl)-phenylazo]-1-napthol-3,6-disulfonic acid;

2-[2-sulfo-5-(2-hydroxysulfonyloxy-ethylsulfonyl)-phenylazo]-1-naphthol-3-sulfonic acid;

1-[2-sulfo-5-(2-hydroxysulfonyloxy-ethylsulfonyl)-phenylazo]-2-naphthol-3,6-disulfonic acid;

1-[2-sulfo-5-(2-hydroxysulfonyloxy-ethylsulfonyl)-phenylazo]-2-naphthol-7-sulfonic acid;

6-dimethylamino-3'-(2-hydroxysulfonyloxy-ethylsulfonyl)-azobenzene-2,6'-disulfonic acid;

4-ethylamino-3'-(2-hydroxysulfonyloxy-ethylsulfonyl)-azobenzene-5,5'-disulfonic acid;

4-ethylamino-3'-methyl-4'-(2-hydroxysulfonyloxy-ethylsulfonyl)-6'-methoxy-azobenzene-5-sulfonic acid;

4-methylamino-3'-methyl-4'-(2-hydroxysulfonyloxy-ethylsulfonyl)-6'-methoxy-azobenzene-5-sulfonic acid;

4-ethylamino-4'-[N-methyl-N-(2-hydroxysulfonyloxy-ethylsulfonyl)-amido]-azobenzene-5-sulfonic acid;

4-methylamino-4'-[N-methyl-N-(2-hydroxysulfonyloxy-ethylsulfonyl)-amido]-azobenzene-5-sulfonic acid;

4-anilino-3'-(2-hydroxysulfonyloxy-ethylsulfonyl)-azobenzene-6'-sulfonic acid;

2-(4-hydroxynaphthyl-1-azo)-4-(2-hydroxysulfonyloxy-ethylsulfonyl)-benzenesulfonic acid; and 4-[N-methyl-N-(2-hydroxysulfonyloxy-ethylsulfonyl)-amido]-2'-dimethylamino-azobenzene-6'-sulfonic acid.

16. A process as defined by claim 1, said dyestuff being selected from the group consisting of 1-[p-(2-hydroxysulfonyloxy-ethylsulfonyl)-phenylazo]-2-naphthol-6,8-disulfonic acid;

1-[2-bromo-4-(2-hydroxysulfonyloxy-ethylsulfonyl)-phenylazo]-2-naphthol-3,6-disulfonic acid;

1-[2-bromo-4-(2-hydroxysulfonyloxy-ethylsulfonyl)-phenylazo]-2-naphthol-6,8-disulfonic acid;

1-[2-bromo-4-(2-hydroxysulfonyloxy-ethylsulfonyl)-phenylazo]-2-naphthol-6-sulfonic acid;

1-[2-nitro-4-(2-hydroxysulfonyloxy-ethylsulfonyl)-phenylazo]-2-naphthol-3,6-disulfonic acid;

2-[2-nitro-4-(2-hydroxysulfonyloxy-ethylsulfonyl)-phenylazo]-1-naphthol-4-sulfonic acid;

1-[2-nitro-4-[2-hydroxysulfonyloxy-ethylsulfonyl)-phenylazo]-2-naphthol-6-sulfonic acid;

1-[2-(2-hydroxysulfonyloxy-ethylsulfonyl)-phenylazo]-2-naphthol-3,6-disulfonic acid;

1-[2,6-dibromo-4-(2-hydroxysulfonyloxy-ethylsulfonyl)-phenylazo]-2-naphthol-3,6-disulfonic acid;

1-[2-chloro-5-(2-hydroxysulfonyloxy-ethylsulfonyl)-phenylazo]-2-naphthol-3,6-disulfonic acid;

1-[2-chloro-5-(2-hydroxysulfonyloxy-ethylsulfonyl)-phenylazo]-2-naphthol-6sulfonic acid;

2-[2-hydroxy-3-nitro-5-(2-hydroxysulfonyloxy-ethylsulfonyl)-phenylazo]-1-naphthol-3,8-disulfonic acid;

2-[2-hydroxy-3-nitro-5-(2-hydroxysulfonyloxy-ethylsulfonyl)-phenylazo]-1-naphthol-3-sulfonic acid;

1-[2-hydroxy-3-nitro-5-(2-hydroxysulfonyloxy-ethylsulfonyl)-phenylazo]-2-naphthol-7-sulfonic acid;

2-(2-sulfo-4-nitrophenylazo)-6-(2-hydroxysulfonyloxy-ethylsulfonyl)-1-naphthol-3-sulfonic acid;

2-[2-hydroxy-6-(2-hydroxysulfonyloxy-ethylsulfonyl)-1-naphthylazo]-5-nitrobenzenesulfonic acid;

2-(2-sulfo-4,6-dinitrophenylazo)-6-[N-methyl-N-(2-hydroxysulfonyloxy-ethylsulfonyl)-amido]-1-naphthol-3-sulfonic acid;

2-(2,4-dinitrophenylazo)-6-[N-methyl-N-(2-hydroxysulfonyloxy-ethylsulfonyl)-amido]-1-naphthol-3-sulfonic acid;

2-[2-nitro-4-(2-hydroxysulfonyloxy-ethylsulfonyl)-phenylazo]-1-naphthol-3,6-disulfonic acid;

2-[2-nitro-4-(2-hydroxysulfonyloxy-ethylsulfonyl)-phenylazo]-1-naphthol-3-sulfonic acid;

1-[2-nitro-4-(2-hydroxysulfonyloxy-ethylsulfonyl)-phenylazo]-2-naphthol-7-sulfonic acid;

1-[2-nitro-4-(2-hydroxysulfonyloxy-ethylsulfonyl)-phenylazo]-2-naphthol-6,8-disulfonic acid; and 2-[2-hydroxy-6-(2-hydroxysulfonyloxy-ethylsulfonyl)-1-naphthylazo]-3,5-dinitrobenzenesulfonic acid.

17. The process of claim 1, wherein said resultant color is compared to a color scale.

18. The process of claim 1, wherein said insoluble polymer carrier is a paper.

19. The process of claim 18, wherein said paper is a cellulosic paper.

20. A process as defined by claim 19 said dystuff being 1-[2-chloro-5-(2-hydroxysulfonyloxy-ethylsulfonyl)-phenylazo]-2-naphthol-3,6-disuifonic acid.

21. A process as defined by claim 19 said dyestuff being 2-(4-hydroxynaphthyl-1-azo)-4-(2-hydroxysulfonyloxy-ethylsulfonyl)-benzenesulfonic acid.

22. A process as defined by claim 19 said dyestuff being 2-[2-nitro-4-(2-hydroxysulfonyloxy-ethylsulfonyl)-phenylazo]-1-naphthol-3,6-disulfonic acid.

23. A process as defined by claim 19 said dyestuff being 1-[2-nitro-4-(2-hydroxysulfonyloxy-ethylsulfonyl)-phenylazo]-2-naphthol-7-sulfonic acid.

24. A process as defined by claim 19 said dyestuff being 4-anilino-3'-(2-hydroxysulfonyloxy-ethylsulfonyl)-azobenzene-6'-carboxylic acid.

25. A process as defined by claim 19 said dyestuff being 4-methylamino-4'-(N-methyl-N-[2-(hydroxysulfonyloxy)-ethyl]-sulfonamido)-azobenzene-5-sulfonic acid.

26. A process as defined by claim 19 said dyestuff being 4-(N-methyl-N-[2-(hydroxysulfonyloxy)-ethyl]-sulfonamido)-2'-dimethylamino-azobenzene-6'-sulfonic acid.

27. A process as defined by claim 19 said dyestuff being 2-(2,4-dinitrophenylazo)-6-(N-methyl-N-[2-(hydroxysulfonyloxy)-ethyl]-sulfonamido)-1-naphthol-3-sulfonic acid.

28. A process as defined by claim 19 said dyestuff being 1-[2-nitro-4-(2-hydroxysulfonyloxy-ethylsulfonyl)-phenylazo]-2-naphthol-6,8-disulfonic acid.

29. A process as defined by claim 19 said dyestuff being 2-(2-sulfo-4,6-dinitro-phenylazo)-6-(N-methyl-N-[2-(hydroxysulfonyloxy)-ethyl]-sulfonamido)-1-naphthol-3-sulfonic acid.

30. A process as defined by claim 19 said dyestuff being 4-(N-methyl-N-[2-(hydroxysulfonyloxy)-ethyl]-sulfonamido)-2'-dimethylamino-azobenzene-6'-carboxylic acid.

31. A process as defined by claim 19 said dyestuff being 4-N-benzyl-N-ethylamino)-3'-(2-hydroxysulfonyloxy-ethylsulfonyl)-azobenzene-6'-carboxylic acid.

32. A process as defined by claim 19 said dyestuff being 4-dimethylamino-3'-(2-hydroxysulfonyloxy-ethylsulfonyl)-azobenzene-6'-carboxylic acid.

33. A process as defined by claim 19 said dyestuff being 4-methylamino-3'-(2-hydroxysulfonyloxy-ethylsulfonyl)-azobenzene-6'-carboxylic acid.

34. A process as defined by claim 19 said dyestuff being 4-ethylamino-5-methyl-3'-(2-hydroxysulfonyloxy-ethylsulfonyl)-azobenzene-6'-carboxylic acid.

35. A process as defined by claim 19 said dyestuff being 4-diethylamino-3'-(2-hydroxysulfonyloxy-ethylsulfonyl)-azobenzene-6'-carboxylic acid.

36. The process of claim 1, wherein said insoluble polymer carrier is microcrystalline cellulose.

37. The process of claim 1, wherein said insoluble polymer carrier is in the form of a powder.

38. A process as defined by claim 1, said dyestuff being 1-[2-chloro-5-(2-hydroxysulfonyloxy-ethylsulfonyl)-phenylazo]-2-naphthol-3,6-disulfonic acid.

39. A process as defined by claim 1, said dyestuff being 2-(4-hydroxynaphthyl-1-azo)-4-(2-hydroxysulfonyloxy-ethylsulfonyl)-benzenesulfonic acid.

40. A process as defined by claim 1, said dyestuff being 2-[2-nitro-4-(2-hydroxysulfonyloxy-ethylsulfonyl)-phenylazo]-1-naphthol-3,6-dixulfonic acid.

41. A process as defined by claim 1, said dyestuff being 1-[2-nitro-4-(2-hydroxysulfonyloxy-ethylsulfonyl)-phenylazo]-2-naphthol-7-sulfonic acid.

42. A process as defined by claim 1, said dyestuff being 4-anilino-3'-(2-hydroxysulfonyloxy-ethylsulfonyl)-azobenzene-6'-carboxylic acid.

43. A process as defined by claim 1, said dyestuff being 4-methylamino-4'-(N-methyl-N-[2-(hydroxysulfonyloxy)-ethyl]-sulfonamido)-azobenzene-5-sulfonic acid.

44. A process as defined by claim 1, said dyestuff being 4-(N-methyl-N-[2-(hydroxysulfonyloxy)-ethyl]-sulfonamido)-2'-dimethylamino-azobenzene-6'-sulfonic acid.

45. A process as defined by claim 1, said dyestuff being 2-(2,4-dinitrophenylazo)-6-(N-methyl-N-[2-(hydroxysulfonyloxy)-ethyl]-sulfonamido)-1-naphthol-3-sulfonic acid.

46. A process as defined by claim 1, said dyestuff being 1-[2-nitro-4-(2-hydroxysulfonyloxy-ethylsulfonyl)-phenylazo]-2-naphthol-6,8-disulfonic acid.

47. A process as defined by claim 1, said dyestuff being 2-(2-sulfo-4,6-dinitro-phenylazo)-6-(N-methyl-N-[2-(hydroxysulfonyloxy)-ethyl]-sulfonamido)-1-naphthol-3-sulfonic acid.

48. A process as defined by claim 1, said dyestuff being 4-(N-methyl-N-[2-(hydroxysulfonyloxy)-ethyl]-sulfonamido)-2'-dimethylamino-azobenzene-6'-carboxylic acid.

49. A process as defined by claim 1, said dyestuff being 4-(N-benzyl-N-ethylamino)-3'-(2-hydroxysulfonyloxy-ethylsulfonyl)-azobenzene-6'-carboxylic acid.

50. A process as defined by claim 1, said dyestuff being 4-dimethylamino-3'-(2-hydroxysulfonyloxy-ethylsulfonyl)-azobenzene-6'-carboxylic acid.

51. A process as defined by claim 1, said dyestuff being 4-methylamino-3'-(2-hydroxysulfonyloxy-ethylsulfonyl)-azobenzene-6'-carboxylic acid.

52. A process as defined by claim 1, said dyestuff being 4-ethylamino-5-methyl-3'-(2-hydroxysulfonyloxy-ethylsulfonyl)-azobenzene-6'-carboxylic acid.

53. A process as defined by claim 1, said dyestuff being 4-diethylamino-3'-(2-hydroxysulfonyloxy-ethylsulfonyl)-azobenzene-6'-carboxylic acid.

* * * * *